United States Patent

Shields

[11] Patent Number: 5,217,029
[45] Date of Patent: Jun. 8, 1993

[54] THERAPEUTIC GLOVE

[76] Inventor: James F. Shields, 4721 W. 184th St., Country Club Hills, Ill. 60478

[21] Appl. No.: 844,441

[22] Filed: Mar. 4, 1992

Related U.S. Application Data

[63] Continuation of Ser. No. 600,908, Oct. 22, 1990, abandoned.

[51] Int. Cl.⁵ .................. A61F 5/37; A63B 23/16
[52] U.S. Cl. ...................... 128/879; 602/62; 482/49; 2/17
[58] Field of Search ............... 128/869, 878, 879, 880, 128/881; 602/20–22, 3, 5, 61–65; 2/16, 17, 158–160; 482/49

[56] References Cited

U.S. PATENT DOCUMENTS

| | | | |
|---|---|---|---|
| 90,389 | 5/1869 | Porter | 602/61 |
| 826,648 | 7/1906 | Challenger | 128/878 |
| 1,377,648 | 5/1921 | Whitaker | 2/158 |
| 2,650,361 | 9/1953 | Grothe et al. | 2/17 |
| 3,476,108 | 11/1969 | Matukas | 128/879 |
| 3,520,539 | 7/1970 | Haws | 2/16 X |
| 3,605,120 | 9/1971 | Hobbs | 2/16 X |
| 3,667,462 | 6/1972 | Moon | 602/62 X |
| 3,741,207 | 6/1973 | Fuson | 2/16 X |
| 3,746,356 | 7/1973 | Shipstad | 2/16 X |
| 3,774,242 | 11/1973 | Owen | 602/21 X |
| 3,888,244 | 6/1975 | Lebold | 602/62 X |
| 4,423,720 | 1/1984 | Meier et al. | 602/62 X |
| 4,469,096 | 9/1984 | Rivadeneyra | 128/879 |
| 4,887,616 | 12/1989 | Baijnath | 128/879 |
| 5,016,648 | 5/1991 | Brown et al. | 128/878 X |
| 5,018,221 | 5/1991 | Romandetto | 128/878 X |
| 5,033,120 | 7/1991 | Myers | 2/16 X |

Primary Examiner—Richard J. Apley
Assistant Examiner—Linda C. M. Dvorak
Attorney, Agent, or Firm—Potthast & Ring

[57] ABSTRACT

An elongate body extending between opposite ends for wrapping around hand of a person in which one of the opposite ends is resiliently releasably clamped to a wrist of a person. The glove also secures the two opposite ends together at the wrist of a person.

21 Claims, 1 Drawing Sheet

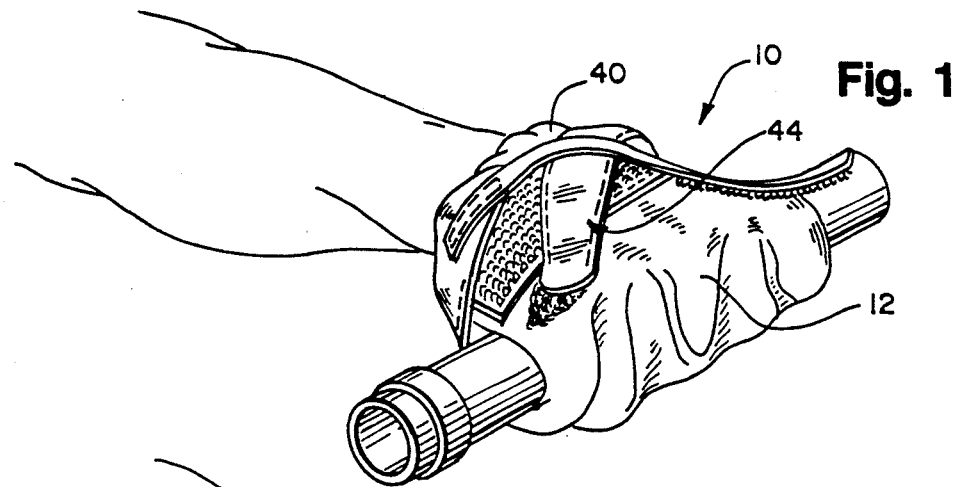
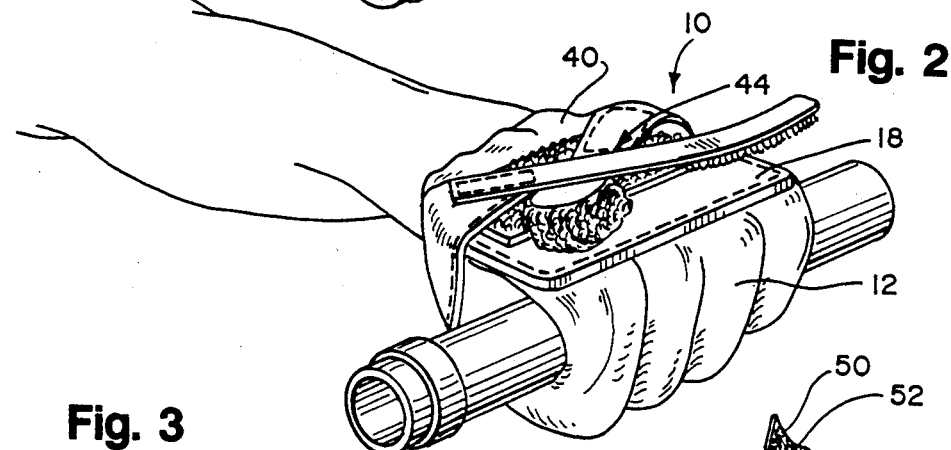
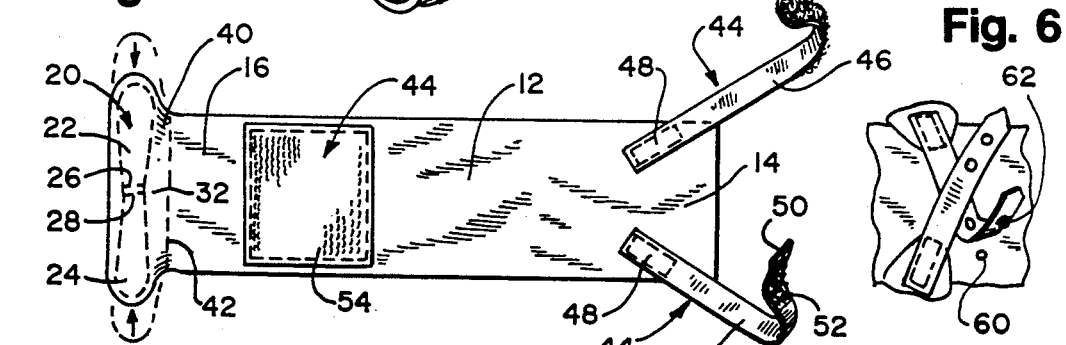
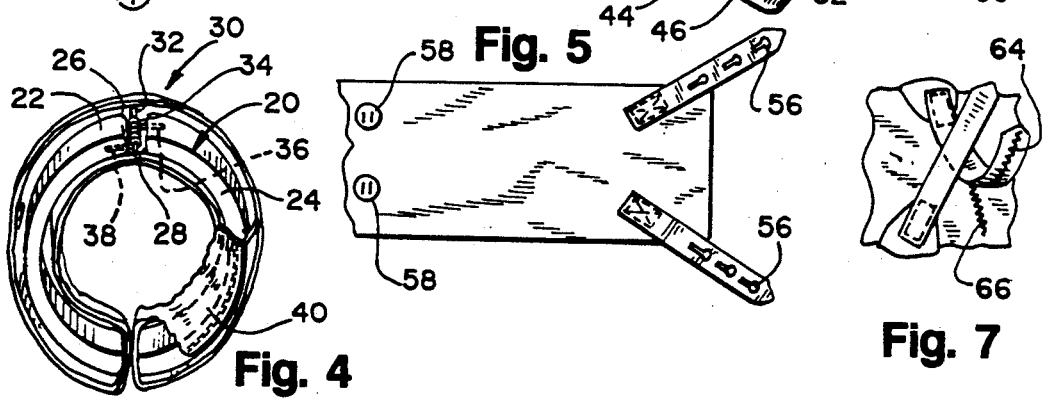

THERAPEUTIC GLOVE

This application is a continuation of application Ser. No. 07/600,908, filed Oct. 22, 1990, now abandoned.

FIELD OF INVENTION

The present invention relates generally to a therapeutic glove for a disabled hand, and more particularly to a therapeutic glove to assist a person in exercising his disabled hand.

BACKGROUND OF THE INVENTION

Persons handicapped by a stroke, Cerebral Palsy, back injury or the like do not have complete control of the fingers or arm or both on a particular side. Needed exercise of these limbs must take place in a clinic or hospital and assistance is needed to get conventional exercise devices onto the disabled hand.

Therapeutic gloves are disclosed in the prior art. In U.S. Pat. No. 3,546,112 issued Dec. 15, 1970, to Courtney is an enclosed glove with compartments for each finger and thumb. Similarly, in U.S. Pat. No. 3,774,242 issued Nov. 27, 1973, to Owen an enclosed compartment for the fingers is provided. These gloves have structures that neglect the condition of the fingers which in the case of a stroke victim are in a state of fisting and cannot be inserted into a digitized glove or envelope easily.

In U.S. Pat. No. 4,447,912, issued May 15, 1984 to Morrow, a glove is provided which does not provide support around the outside of the fingers of the disabled hand; has a hole that the thumb must be fitted through; and straps are wrapped about the wrist in securing the device.

In U.S. Pat. No. 4,698,850, issued Oct. 13, 1987 to Patton et al., provides a hole that the thumb must be fitted through and utilizes straps wrapped about the wrist in securing the glove.

SUMMARY OF THE INVENTION

It is an object of this invention to provide a therapeutic glove which can be easily put on or taken off the inflicted hand.

It is an object of this invention to provide securement support of the entire hand about an exercise device.

It is an object of this invention to provide a therapeutic glove which has an elongate body extending between opposite ends for wrapping around a hand of a person and means for resiliently releasably clamping one of said opposite ends to a wrist of a person.

It is another object of this invention to provide a therapeutic glove which has an elongate body extending between opposite end portions for wrapping around a hand of a person and means for securing the opposite end portions at a wrist of a person.

BRIEF DESCRIPTION OF THE DRAWINGS

The foregoing objects and advantageous features of the invention will be explained in greater detail and others will be made apparent from the detailed description of the preferred embodiment of the present invention which is given with reference to the several figures of the drawing, in which:

FIG. 1 is a perspective view of one of the embodiments of the therapeutic glove as worn;

FIG. 2 is a perspective view of another of the embodiments of the therapeutic glove as worn;

FIG. 3 is a plan view of the therapeutic glove of the embodiment shown in FIG. 1;

FIG. 4 is a partial cut away view of the resilient clamping means for clamping the therapeutic glove to a person's wrist;

FIG. 5 is a partial plan view of the therapeutic glove in FIG. 3 showing an alternative embodiment of securement;

FIG. 6 is a partial perspective view of an alternative embodiment of securement as shown in FIG. 5, as worn; and FIG. 7 is a partial perspective view of an alternative embodiment of securement as shown in FIG. 5, as worn.

DETAILED DESCRIPTION

Referring now to the drawings, therapeutic glove 10 has an elongate body 12, as seen in FIG. 3. Elongate body 12 has opposite ends or end portions 14 and 16.

Body 12 is a piece of flexible material such as leather, which will be nonabrasive to the skin on a person's hand. Body 12 is of a sufficient length in order to wrap it around a person's hand, as seen in FIG. 1. An alternative embodiment of body 12 can be seen in FIG. 2. In this embodiment a substantially rigid portion 18, such as stiffened leather, plastic or the like, which overlies the back of a person's hand between the wrist and the first knuckle. The remainder of body 12 is of a flexible material, such as leather.

A resiliently releasable clamping means 20, as seen in FIGS. 3 and 4, provide ease in attaching elongate body 12 to a person's wrist. Clamping means 20, as seen in FIG. 4, includes two arcuate segments 22 and 24. Segments 22 and 24 each have ends 26 and 28 respectively that are attached by biasing means 30, as seen in FIG. 4.

Biasing means 30 typically will include a hinge 32 which will have a torsion spring 34 associated with or attached to hinge 32. Torsion spring 34 has an arm 36 which influences arcuate segment 24 toward the other arcuate segment 22 and has an arm 38 which influences other arcuate segment 22 toward arcuate segment 24. This structure forms substantially a ring which can be opened and closed. This structure provides ease in mounting elongate body 12 to the wrist of a disabled person with one hand. Clamping means 20 can be opened with one hand and easily slipped over the disabled wrist where clamping means 20 can be released and closed about the wrist.

Clamping means 20 is typically enclosed in a sleeve 40 having closed ends. Sleeve 40 is composed of a flexible material, again, such as leather. Further, sleeve 40 is sewn or conventionally attached to elongate body 12 as seen by stitching 42, in FIG. 3. This enclosure of clamping means 20 by closed tube 40 made of a flexible material, protects the wrist of the user from irritation.

Elongate body 12 is wrapped about the disabled hand as seen in FIGS. 1 and 2. Elongate body 12 is sideless as seen in FIG. 3. Thus, typically the user will secure one end 16 of elongate body 12 to his wrist with clamping means 20 and wrap elongate body 12 around the hand. End 14 of elongate body 12 must then be secured to elongate body 12 and keep body 12 secured about the hand. Securing means 44 is provided to secure ends 14 and 16 together to secure the hand.

Securing means 44, comprises at least one flexible strap 46, as seen in FIG. 3, in which a first end 48 is attached to elongate body 12 at end 14 and having a second end 50, having a first releasable engaging element 52. Further, a second releasable engaging element 54 is attached to the opposite end portion 16 of elongate body 12, as seen in FIG. 3. Thus, elongate body 12 is wrapped about the disabled hand, after being attached to the wrist, and opposite ends 14 and 16 of elongate body are releasably engaged by releasable securing means 44, securing the hand.

Various embodiments of securing means 44 are shown. In FIG. 3, first releasable engaging element 52 is a hook/loop pad, and second releasable engaging element 54 is also a hook/loop pad. Thus, first and second releasable engaging elements 52 and 54 will matingly engage one another with a slight pressure being applied between the elements.

Another embodiment of securing means 44 is shown in FIG. 5, in which releasable engaging elements 52 and 54 are at least a loop 56 and at least a button 58. These elements are interchangeable as to location.

Another embodiment of securing means 44 is shown in FIG. 6, in which releasable engaging elements 52 and 54 are at least one mating arrangement of a male and female snap fit members 60 and 62 respectively. Once again these elements are interchangeable as to location.

Finally, another embodiment of securing means 44 is shown in FIG. 7, in which releasable engaging elements 52 and 54 are at least a hook and a loop 64 and 66 respectively. Once again these elements are interchangeable as to location.

While a detailed description of the preferred embodiments of the invention has been given it should be appreciated that many variations can be made there to without departing from the scope of the invention as set forth in the appended claims.

I claim:

1. A therapeutic glove comprising:
    an elongate body extending between opposite end for wrapping around and substantially enclosing a plurality of fingers and a thumb of a hand of a person; and
    means for resiliently releasably clamping one of said opposite ends to a wrist of a person, said means being secured to the elongate body and further wherein said means includes biasing means.

2. The apparatus in claim 1 in which the elongate body is a piece of flexible material of sufficient length to encompass a hand of a person.

3. The apparatus in claim 2 in which the flexible material is leather.

4. The apparatus in claim 1 in which the elongate body portion has a substantially rigid portion that overlies a portion of the back of a person's hand between a person's wrist and first knuckles.

5. The apparatus of claim 4 in which the remainder of said body portion is a flexible material.

6. The apparatus of claim 1 in which said clamping means comprises an arcuate segment having an end and another arcuate segment having an end in which said ends are attached by said biasing means, wherein said biasing means biases said arcuate segments toward one another forming substantially a ring which can be opened and closed.

7. The apparatus of claim 6 in which said biasing means includes a hinge associated with a torsion spring having two arms in which one arm influences said arcuate segments toward one another.

8. The apparatus of claim 6 in which said annular segments are enclosed by a tubular sleeve having both ends of the tube closed thereby encasing said arcuate segments.

9. The apparatus of claim 8 in which said sleeve is composed of a flexible material.

10. The apparatus of claim 8 in which said sleeve is attached to said elongate body.

11. A therapeutic glove, comprising:
    an elongate body extending between two opposite end portions for wrapping around and substantially enclosing a plurality of fingers and a thumb of a person's hand;
    means for securing the two end portions together at a wrist of a person; and
    means for resiliently releasably clamping one of said opposite ends to a person's wrist, said means being attached to said elongate body at said one of said opposite ends.

12. The apparatus of claim 11 in which the elongate body is a piece of flexible material of sufficient length to encompass a hand of a person.

13. The apparatus of claim 12 in which the flexible material is leather.

14. The apparatus of claim 11 in which the elongate body has a substantially rigid portion that overlies a portion of the back of a person's hand between a person's wrist and first knuckles.

15. The apparatus of claim 11 in which said clamping means comprises an arcuate segment having an end and another arcuate segment having an end in which said ends are attached by means for biasing said arcuate segments toward one another forming substantially a ring which can be opened and closed.

16. The apparatus of claim 15 in which said biasing means includes a hinge associated with a torsion spring having two arms in which one arm influences said arcuate segments toward one another.

17. The apparatus of claim 11 in which securing means includes:
    at least one flexible strip having a first and second end in which said first end is attached to one end portion of said elongate body and said second end has a first releasable engaging element and
    a second releasable engaging element attached to the other opposite end portion of said elongate body which will releasably engage said first releasable engaging element.

18. The apparatus of claim 17 in which said first and second releasable engaging elements are mating arrangement of hook/loop pads.

19. The apparatus of claim 17 in which said first and second releasable engaging elements are mating arrangement of male and female snap fit members.

20. The apparatus of claim 17 in which said first and second releasable engaging elements are a mating arrangement of a button and loop.

21. The apparatus of claim 17 in which said first and second releasable engaging elements are a mating array of hooks and loops.

* * * * *

UNITED STATES PATENT AND TRADEMARK OFFICE
CERTIFICATE OF CORRECTION

PATENT NO. : 5,217,029

DATED : June 8, 1993

INVENTOR(S) : James F. Shields

It is certified that error appears in the above-identified patent and that said Letters Patent is hereby corrected as shown below:

Col. 3, line 36, change "end" to --ends--.

Signed and Sealed this

First Day of February, 1994

*Attest:*

BRUCE LEHMAN

*Attesting Officer*     *Commissioner of Patents and Trademarks*